(12) United States Patent
Voic et al.

(10) Patent No.: US 11,540,853 B2
(45) Date of Patent: Jan. 3, 2023

(54) ULTRASONIC SURGICAL INSTRUMENT AND METHOD FOR MANUFACTURING SAME

(71) Applicant: MISONIX, INC., Farmingdale, NY (US)

(72) Inventors: Dan Voic, Cedar Grove, NJ (US); Scott Isola, Deer Park, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 547 days.

(21) Appl. No.: 16/540,532

(22) Filed: Aug. 14, 2019

(65) Prior Publication Data
US 2019/0374245 A1      Dec. 12, 2019

Related U.S. Application Data

(62) Division of application No. 15/147,323, filed on May 5, 2016, now Pat. No. 10,405,875.

(51) Int. Cl.
| | | |
|---|---|---|
| *A61B 17/32* | (2006.01) | |
| *B23P 15/28* | (2006.01) | |
| *A61B 17/00* | (2006.01) | |

(52) U.S. Cl.
CPC ...... *A61B 17/320068* (2013.01); *B23P 15/28* (2013.01); *A61B 2017/00526* (2013.01); *A61B 2017/320069* (2017.08); *A61B 2017/320072* (2013.01); *A61B 2017/320074* (2017.08); *A61B 2017/320075* (2017.08); *A61B 2017/320077* (2017.08); *A61B 2217/007* (2013.01)

(58) Field of Classification Search
CPC .............................................. A61B 17/320068
See application file for complete search history.

(56) References Cited

U.S. PATENT DOCUMENTS

| | | | | |
|---|---|---|---|---|
| 2,349,959 | A * | 5/1944 | Guetzkow | B23B 31/107 409/232 |
| 2,753,666 | A * | 7/1956 | Sasse | B24B 3/38 451/224 |
| 5,180,363 | A * | 1/1993 | Idemoto | B06B 3/00 604/22 |
| 5,695,510 | A | 12/1997 | Hood | A61B 17/320068 30/355 |
| 6,436,114 | B1 | 8/2002 | Novak | A61L 317/320092 606/169 |
| 6,443,969 | B1 * | 9/2002 | Novak | A61B 17/320068 606/169 |
| 8,894,673 | B2 | 11/2014 | Darian | A61B 17/320068 606/169 |
| 10,016,208 | B2 | 7/2018 | Gouery | A61B 17/320068 |

(Continued)

*Primary Examiner* — Zade Coley
(74) *Attorney, Agent, or Firm* — R. Neil Sudol; Henry D. Coleman

(57) ABSTRACT

An ultrasonic surgical instrument comprises a cylindrical shaft and a blade at a distal or free end of the shaft, the blade being unitary and continuous with the shaft, without an intervening joint. The shaft has a longitudinal axis and the blade includes a flat or planar blade body with a proximal end eccentrically disposed relative to the shaft axis. Thus, the blade body or at least a proximal end portion thereof is disposed eccentrically relative to the shaft. The blade in its entirely may be inclined relative to the shaft axis or extend parallel thereto.

8 Claims, 5 Drawing Sheets

(56) References Cited

U.S. PATENT DOCUMENTS

| | | | |
|---|---|---|---|
| 2008/0234710 A1* | 9/2008 | Neurohr | A61B 17/320068 606/169 |
| 2013/0204285 A1* | 8/2013 | Gouery | A61B 17/320068 606/169 |
| 2014/0358043 A1* | 12/2014 | Akagane | A61B 17/320068 601/2 |
| 2016/0166276 A1 | 6/2016 | Huang | A61B 17/1644 606/169 |

* cited by examiner

ULTRASONIC SURGICAL INSTRUMENT AND METHOD FOR MANUFACTURING SAME

CROSS-REFERENCE TO RELATED APPLICATION

This application is a division of application Ser. No. 15/147,323 filed May 5, 2016, now U.S. Pat. No. 10,405,875.

BACKGROUND OF THE INVENTION

This invention relates to an ultrasonic surgical tool or instrument. This invention also relates to a method for manufacturing the tool or instrument.

U.S. Pat. No. 6,379,371 discloses an ultrasonic surgical blade, particularly for cutting bone tissue, which has a blade body with a smooth continuous cutting edge and a shank connected at one end to the blade body and operatively connectable at an opposite end to a source of ultrasonic vibrations. The shank is provided with an axially extending bore for the conveyance of cooling fluid to the cutting edge, while the blade body is provided with an axially extending through-slot communicating at one end with the bore. The blade body is preferably provided at an end opposite the shank with a recess communicating, with the bore for distributing fluid from the slot towards the cutting edge. The recess preferably has a configuration which parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

In the manufacture of such a bone-cutting instrument, the blade body is generated separately and then affixed to the end of a tubular shaft. Thus there is a joint between the instrument shaft or horn and the blade.

OBJECTS OF THE INVENTION

It is an object of the present invention to provide an improved ultrasonic instrument particularly a bone-cutting blade.

Another object of the present invention is to provide such a tool or instrument wherein joints are reduced if not eliminated.

A further object of the present invention is to provide such a tool or instrument wherein manufacture is facilitated.

It is a concomitant object of the present invention to provide such a tool or instrument which may be produced at less expense than existing instruments.

Yet another object of the present invention is to provide a method for manufacturing an ultrasonic bone cutting instrument or tool.

These and other objects of the invention will be apparent to those skilled in the art from the drawings and descriptions hereof. Although each object is attained by at least one embodiment of the invention, no embodiment need necessarily meet every object.

SUMMARY OF THE INVENTION

An ultrasonic surgical instrument in accordance with the present invention comprises a cylindrical shaft and a blade at a distal or free end of the shaft, the blade being unitary and continuous with the shaft, without an intervening joint. As discussed hereinafter, the manufacture of this instrument entails machining a distal end of a tool blank and particularly a distal end portion of a shaft thereof.

The surgical instrument typically further comprises a radially or transversely enlarged proximal end portion at a proximal end of the shaft opposite the blade. The enlarged proximal end portion is configured for attachment to an electromechanical transducer device such as a piezo-electric stack housed inside an instrument hand piece.

Pursuant to a further feature of the present invention, the shaft has a longitudinal axis and the blade includes a flat or planar blade body with a proximal end eccentrically disposed relative to the shaft axis. Thus, the blade body or at least a proximal end portion thereof is disposed eccentrically relative to the shaft.

Pursuant to another feature of the present invention, the blade body has at least one edge or peripheral surface that is a cylindrical section continuous and coaxial with a cylindrical outer surface of the shaft.

In one embodiment of the present invention, the blade body extends in a plane parallel to the shaft axis.

The shaft has an end face contiguous with the proximal end of the blade body and also has a channel or bore with an outlet in the end face.

According to another aspect of the present invention, where the blade body has a major lateral surface facing the axis, the blade body is provided in the major lateral surface with a groove continuous with the channel or bore at the outlet thereof. The groove may extend the length of the blade body to a distal end of the blade body. Alternatively, where the blade body is provided with a through slot or hole, the groove extends from the outlet of the shaft channel or bore to a proximal side of the through slot or hole.

The blade body may be provided at a distal end, opposite the shaft, with a beveled surface inclined with respect to the axis. Alternatively or additionally, the blade body may be formed with an arcuate distal tip, where the distal tip has a circular or cylindrical surface with an axis oriented perpendicular to the shaft axis.

In a second embodiment of the present invention, the blade body extends at an angle with respect to the axis and intersecting the shaft axis. Where the shaft has an end face contiguous with the proximal end of the blade body and additionally has a channel or bore with an outlet in the end face, the blade body has a planar first major lateral surface and a planar second major lateral surface facing oppositely to one another.

Pursuant to another feature of the present invention, the blade body is provided in the first major lateral surface with a groove continuous with the channel or bore at the outlet. The blade body may be further provided with a through hole at an end of the groove opposite the end face and the outlet, the groove extending from the outlet to the through hole. The second major lateral surface may formed with an additional groove communicating with the through hole. The additional groove is preferably tapered from a wide end at the through hole and a closed narrow end at the second major lateral surface. The second major lateral surface may take the form of an annular oval surface with an oval center edge formed by the through hole and the additional groove.

The blade body of this second embodiment may have an endless peripheral or perimetric surface continuous with a cylindrical outer surface of the shaft, the peripheral or perimetric surface being a cylindrical section coaxial with the outer surface of the shaft.

The present invention is also directed to a method for manufacturing a unitary ultrasonic surgical instrument having a shaft portion and a blade portion at a distal of free end of the shaft, the blade being unitary and continuous with the shaft, without an intervening joint. The method comprises providing a tool blank including an enlarged connector portion at one end and a cylindrical shaft at an opposite end and machining a distal end portion of the cylindrical shaft on opposing sides thereof to form the shaft portion from the cylindrical shaft and to generate two opposing flats. The formation of the flats may realize the blade portion as a planar shaft extension or end portion having at least one edge surface that is a cylindrical section continuous and coaxial with a cylindrical outer surface of the shaft portion.

The machining of the distal end portion of the cylindrical shaft preferably includes rotating a cutting tool about a rotation axis extending parallel to at least one of the flats.

The machining of the distal end portion of the cylindrical shaft typically includes forming an end surface of the shaft portion as a cylindrical section having an axis parallel to the rotation axis and one or both flats.

The present invention provides an ultrasonic instrument, particularly an ablation or bone-cutting instrument that is more easily manufactured and that can have tighter or more consistent specifications. Thus quality control is facilitated.

DETAILED DESCRIPTION

Figure 1:
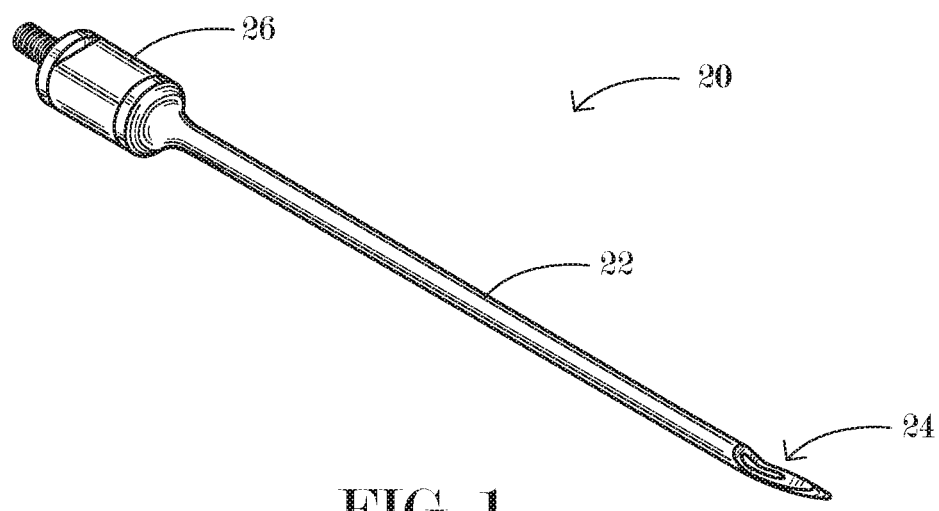
FIG. 1 is an isometric view of an ultrasonic surgical instrument or probe pursuant to the present invention.

Each of the ultrasonic surgical instrument embodiments illustrated in the drawings comprises a cylindrical shaft and a blade at a distal of free end of the shaft, the blade being unitary and continuous with the shaft, without an intervening joint. The manufacture of these instruments entails machining a distal end of a tool blank and particularly a distal end portion of a tubular shaft thereof.

As depicted in FIG. 1, a surgical instrument 20 comprises a cylindrical shaft 22 and a blade 24 at a distal or free end of the shaft, the blade being unitary and continuous with the shaft, without an intervening joint. Instrument 20 (and all of the instruments disclosed herein) typically further comprises a radially or transversely enlarged proximal end portion 26 at a proximal end of the shaft 22 opposite blade 24. Proximal end portion 26 is configured for attachment to an electro-mechanical transducer device (not shown) such as a piezoelectric stack housed inside an instrument hand piece (not shown).

Shaft 22 has a longitudinal axis 28 and blade 24 includes a flat or planar blade body 30 with a proximal end 32 eccentrically disposed relative to shaft axis 28. Thus, blade body 30 or at least a proximal end portion thereof is disposed eccentrically relative to shaft 28.

In each embodiment of an ultrasonic surgical instrument disclosed herein, a blade includes a flat or planar blade body with a proximal end eccentrically disposed relative to a shaft axis. Thus, the blade body or at least a proximal end portion thereof is disposed eccentrically relative to the instrument shaft.

Figure 2:
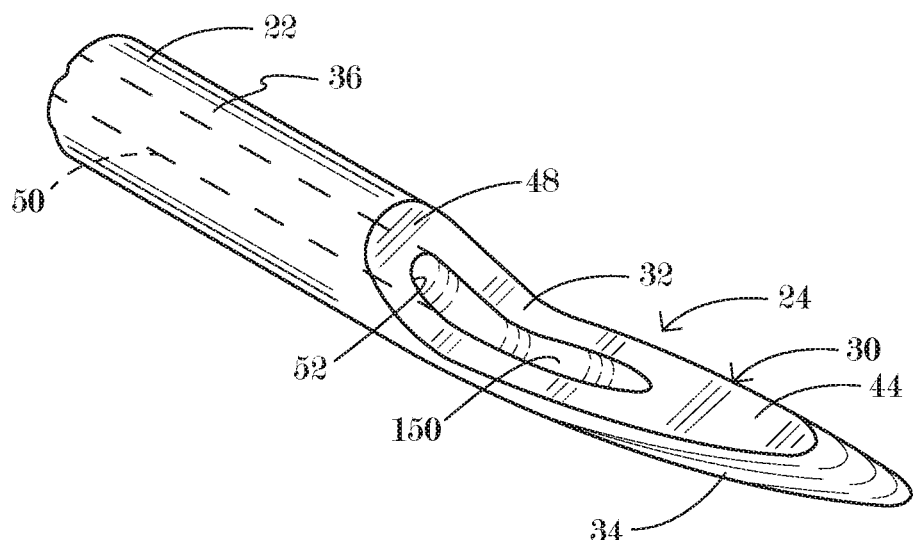
FIG. 2 is an isometric view, on a larger scale, of a distal end portion of the instrument or probe of FIG. 1.
Figure 3:
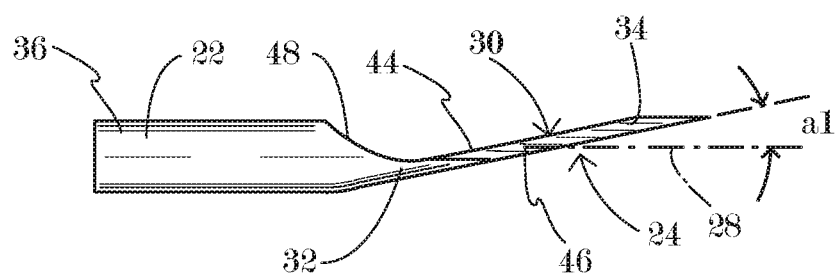
FIG. 3 is a side elevational view of the distal end portion of FIG. 2.
Figure 4:
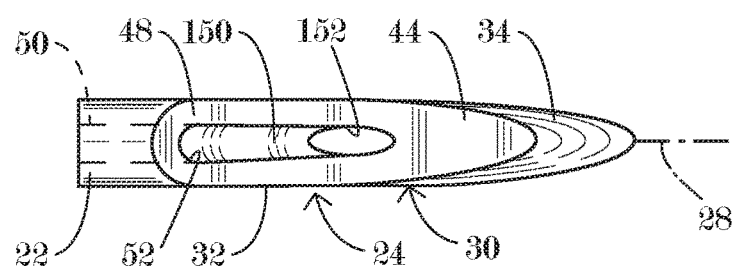
FIG. 4 is a top plan view of the distal end portion of FIGS. 2 and 3.

As illustrated In FIGS. 2-4, blade body 30 has at least one edge or peripheral surface 34 that is an endless cylindrical section or perimetral surface continuous and coaxial with a cylindrical outer surface 36 of shaft 22.

Each embodiment of an ultrasonic surgical instrument disclosed herein has a blade body with at least one edge or peripheral surface in the form of a cylindrical section continuous and coaxial with a cylindrical outer surface of the instrument shaft.

Figure 5:
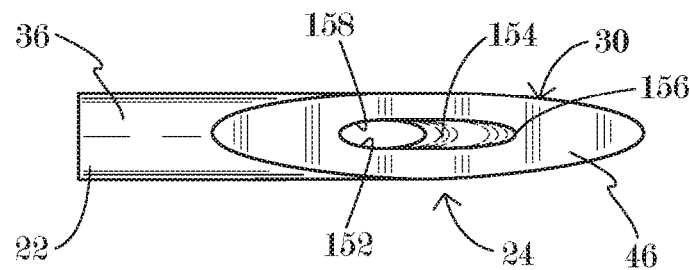
FIG. 5 is a bottom plan view of the distal end portion of FIGS. 2-4.
Figure 6:
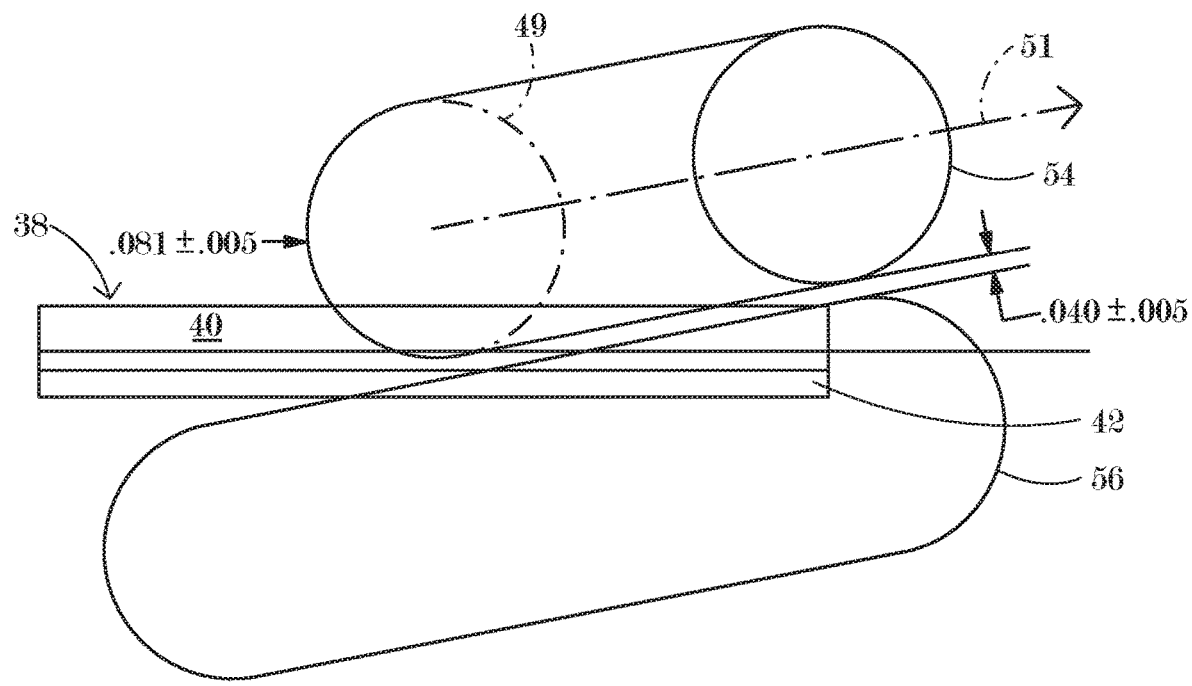
FIG. 6 is a longitudinal cross-sectional view of a tubular tool blank schematically illustrating two envelopes of cutting tool paths on an upper side and a lower side, in a method for manufacturing the instrument or probe of FIGS. 1-5, in accordance with the present invention.

As illustrated in FIG. 6, a method for manufacturing surgical instrument 20 comprises providing a tool blank 38 including an enlarged connector portion 26 (FIG. 1) at one end and a cylindrical shaft 40 at an opposite end and machining a distal end portion 42 of the cylindrical shaft on opposing sides (not designated) thereof to form the shaft portion 22 (FIG. 1) of instrument 20 from cylindrical shaft 40 of the blank 38 and to generate two opposing flats or major blade surfaces 44 and 46. The formation of flats 44 and 46 realizes the blade portion 24 (FIGS. 1-5) as a planar shaft extension or end portion having edge or peripheral surface 34.

As illustrated in FIG. 3, blade body 30 extends at an angle a1 with respect to shaft axis 28 and intersects the shaft axis. Blade body 30 is a planar shaft extension machined down from an end portion of a cylindrical blank so that the blade body extends only within a cylindrical envelope, inclusive of the cylindrical envelope, that is coaxial and co-cylindrical with the cylindrical outer surface 36 of shaft 22. Blade body 30 extends across a first cylinder that is co-cylindrical with the inner surface of shaft 22 defining bore or channel 50. A distal terminal portion (not designated) of blade body 30 is located entirely between (and inclusive of) that inner first cylinder, co-cylindrical with bore or channel 50, and the cylindrical envelope (an outer second cylinder) that is co-cylindrical with outer surface 36 of shaft 22, the terminal portion being continuous without break or interruption. Shaft 22 has an end face 48 contiguous with the proximal end 32 of blade body 30 and additionally has a channel or bore 50 with an outlet 52 in the end face 48. Flats 44 and 46 are a planar first major lateral surface and a planar second major lateral surface facing oppositely to one another.

It is to be noted that a rotating cutting tool (schematically depicted at 49) is used to cut flats 44 and 46 from distal end portion 42 (FIG. 6) of blank 38. The rotating cutting tool has a circular or cylindrical cutting face (not separately designated) that is moved along a first linear path 51 (FIG. 6) so as to exhibit an oblate oval cutting envelope 54, as shown in FIG. 6. Shaft end face 48 is formed simultaneously with the formation of a proximal end portion of flat 44 by the same cutting action and accordingly takes the form of a cylindrical section. Of course, end face 48 may be separately and additionally machined in a supplemental process to provide the end face with a planar form.

The same rotating cutting tool 49 may be used to form lower flat 46, as schematically indicated by another oblate oval cutting envelope 56, as shown in FIG. 6.

As depicted in FIGS. 2 and 4, blade 24 is provided in flat or major lateral surface 44 with a groove 150 continuous with a channel or bore 50 at outlet 52. Blade 24 is further formed so as to exhibit a through hole 152 at an end of groove 150 opposite end face 48 and outlet 52. Groove 150 extends from outlet 52 to through hole 152. As shown in FIG. 5, flat or major lateral surface 46 is formed with an additional groove 154 communicating with through hole 152. Groove 154, continuous and communicating with through hole 152, is disposed on a side of the through hole opposite outlet 52 and the distal or free end of shaft 22. Groove 154 has a distal end (not designated) spaced from a distal tip (not designated) of blade body 30, the distal tip being closed and continuous, without break or interruption. Groove 154 is tapered from a wide end at through hole 152 and a closed narrow end 156 at flat or major lateral surface 46. Surface 46 is in the form of an annular oval surface with an oval center edge 158 formed by through hole 152 and groove 154.

In each of the embodiments of FIGS. 7-16, a blade extends parallel to an axis of an elongate linear instrument shaft and to one side of that axis. Accordingly, each blade body necessarily has a proximal end that is unitary with the distal end of the shaft at a point that is eccentrically disposed relative to the shaft, i.e., at a distance from the shaft axis. The various blades are produced by machining a blank in the form of a tubular rod with a cutting tool having a circular cutting edge or cylindrical cutting surface, with that cutting tool being moved along a path parallel to the shaft axis. The distal end faces of the shafts may have a cylindrically concave surface produced by the circular or cylindrical cutting tool or may be flat as illustrated, which shape is rendered by further machining, for instance, by moving the circular or cylindrical cutting surface along a linear path at an angle from the shaft axis.

Figure 7:
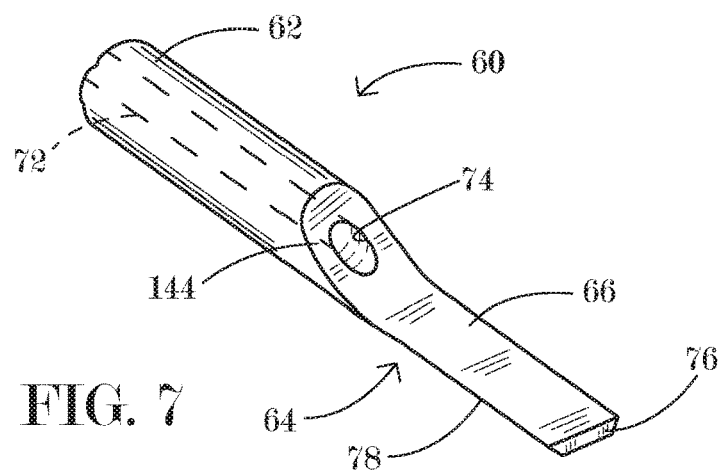
FIG. 7 is an isometric view of a distal end portion of another ultrasonic surgical instrument or probe pursuant to the present invention.
Figure 8:
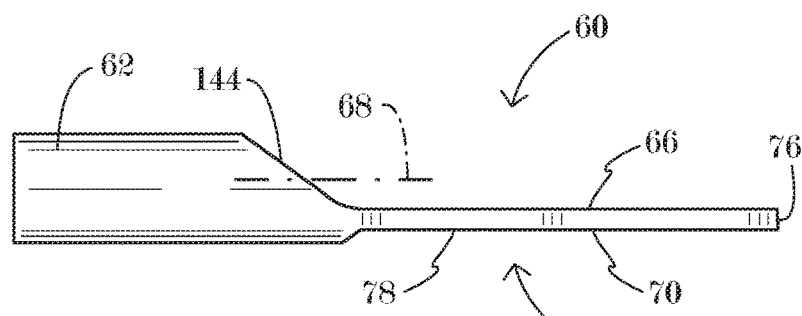
FIG. 8 is a side elevational of the distal end portion of FIG. 7.

As depicted in FIGS. 7 and 8, a surgical instrument 60 comprises a cylindrical shaft 62 and a blade 64 at a distal or free end of the shaft, the blade being unitary and continuous with the shaft, without an intervening joint. Instrument 60 further comprises a radially or transversely enlarged proximal end portion 26 (FIG. 1) at a proximal end of the shaft 62 opposite blade 64 or connecting to an electromechanical transducer device (not shown) such as a piezo-electric stack housed inside an instrument hand piece (not shown).

Blade 64 has a planar upper major surface 66 facing an axis 68 of instrument shaft 62 and a planar lower major surface 70 facing in the opposite direction, away from axis 68. Surfaces 66 and 70 are parallel to one another and to axis 68. Blade 64 is spaced at such a distance from axis 68 that no groove is formed in upper surface 66. A channel or lumen 72 of shaft 62 has an outlet port 74 over a proximal end of surface 66 so that irrigant flowing under pressure through the channel or lumen empties out onto surface 66. Blade 64 has a distal end face 76 that is flat and oriented perpendicularly to shaft axis 68. Blade 64 has a pair of lateral peripheral edge surfaces 78 that are cylindrical sections continuous and coaxial with an outer surface (not separately designated) of shaft 62.

Figure 9:
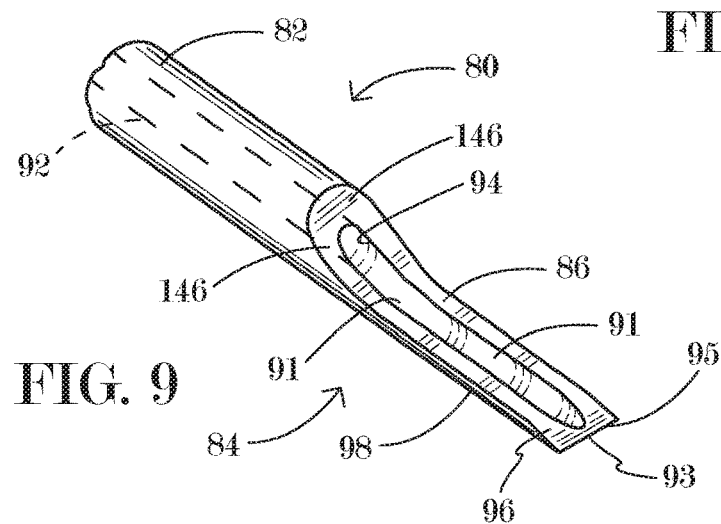
FIG. 9 is an isometric view of a distal end portion of a further ultrasonic surgical instrument or probe pursuant to the present invention.
Figure 10:
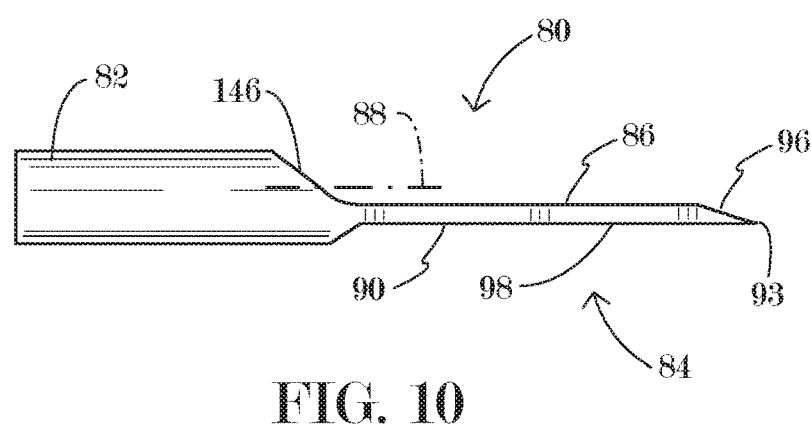
FIG. 10 is a side elevational view of the distal end portion of FIG. 9.

As illustrated in FIGS. 9 and 10, a surgical instrument 80 comprises a cylindrical shaft 82 and a blade 84 at a distal or free end of the shaft, the blade being unitary and continuous with the shaft, without an intervening joint. Instrument 80 further comprises a radially or transversely enlarged proximal end portion 26 (FIG. 1) at a proximal end of the shaft 82 opposite blade 84 or connecting to an electromechanical transducer device (not shown) such as a piezo-electric stack housed inside an instrument hand piece (not shown).

Blade 84 has a planar upper major surface 86 facing an axis 88 of instrument shaft 82 and a planar lower major surface 90 facing in the opposite direction, away from axis 88. Surfaces 86 and 90 are parallel to one another and to axis 88. Blade 84 is spaced at such a distance from axis 68 that an elongate groove 91 is formed in upper surface 86. Groove 91 is continuous and coaxial with a cylindrical surface (not separately designated) of a channel or lumen 92 of shaft 82 and communicates with the channel or lumen via an outlet port 94 thereof. During use of the instrument 80, irrigant flows under pressure through channel or lumen 92 and empties into groove 91, from which the irrigant is distributed over surface 86. Blade 84 has a beveled distal end face 96 that is flat with a straight terminal edge 93 and rounded corners 95 and oriented at an angle to shaft axis 88. Groove 91 terminates in or at beveled distal end face 96. Blade 84 has a pair of lateral peripheral edge surfaces 98 that are cylindrical sections continuous and coaxial with an outer surface (not separately designated) of shaft 82.

Figure 11:
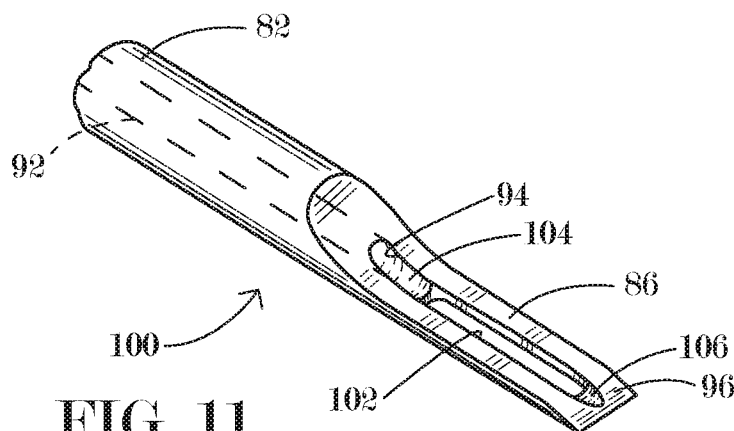
FIG. 11 is an isometric view of a distal end portion of an additional ultrasonic surgical instrument or probe pursuant to the present invention.
Figure 12:
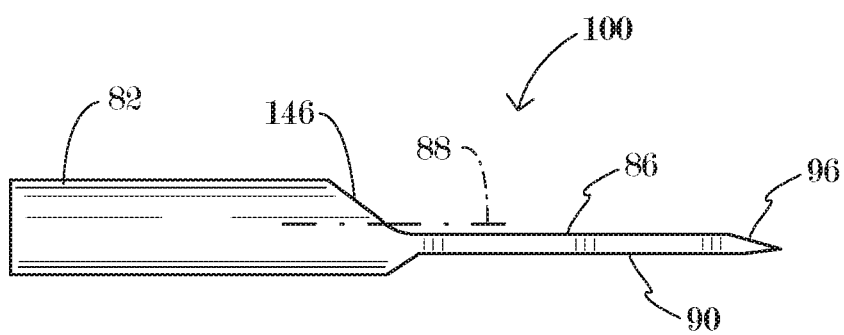
FIG. 12 is a side elevational view of the distal end portion of FIG. 11.

FIGS. 11 and 12 depict a surgical instrument 100 that is identical to instrument 80 except for the provision of a through slot 102 in blade 84. Reference numbers in FIGS. 11 and 12 are the same as those designating like features or elements of surgical instrument 80. Slot 102 is formed in groove 91, essentially midway along the length thereof, and divides the groove into a proximal groove segment 104 and a distal groove segment 106. Slot 102 facilitates the flow of irrigant from groove 91 or groove segment 104 to under surface 90.

Figure 13:
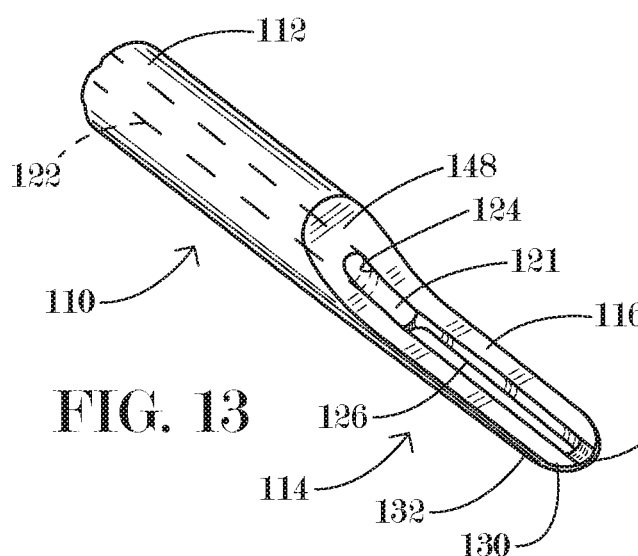
FIG. 13 is an isometric view of a distal end portion of yet another ultrasonic surgical instrument or probe pursuant to the present invention.
Figure 14:
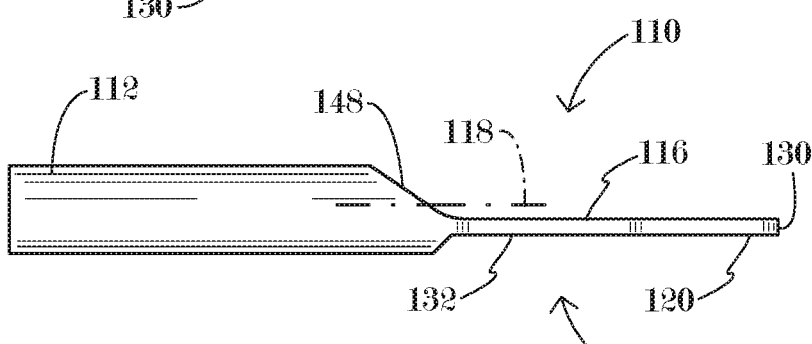
FIG. 14 is a side elevational of the distal end portion of FIG. 13.

As shown in FIGS. 13 and 14, a surgical instrument 110 comprises a cylindrical shaft 112 and a blade 114 at a distal or free end of the shaft, the blade being unitary and continuous with the shaft, without an intervening joint. Instrument 110 further comprises a radially or transversely enlarged proximal end portion 26 (FIG. 1) at a proximal end of the shaft 112 opposite blade 114 or connecting to an electromechanical transducer device (not shown) such as a piezo-electric stack housed inside an instrument hand piece (not shown).

Blade 114 has a planar upper major surface 116 facing an axis 118 of instrument shaft 112 and a planar lower major surface 120 facing in the opposite direction, away from axis 118. Surfaces 116 and 120 are parallel to one another and to axis 118. Blade 114 is spaced at such a distance from axis 118 that a short groove section 121 is formed in upper surface 116, where the groove section is continuous and coaxial with a cylindrical surface (not separately designated) of a channel or lumen 122 of shaft 112 and communicates with the channel or lumen via an outlet port 124 thereof. Blade 114 is also provided with an elongate through slot 126 extending parallel to shaft axis 118. At a distal end of through slot 126, blade 114 has a distal groove section 128 that extends from slot 126 on one side to a circular edge or cylindrical end surface 130 on an opposite side. Blade 114 has a pair of lateral peripheral edge surfaces 132 that are cylindrical sections continuous and coaxial with an outer surface (not separately designated) of shaft 112.

During use of the instrument 110, irrigant flows under pressure through channel or lumen 122 and into proximal groove section 121 and then into slot 126 from which the irrigant may exit onto both major blade surfaces 116 and 120 and to circular edge or cylindrical end surface 130.

Figures 15, 16:
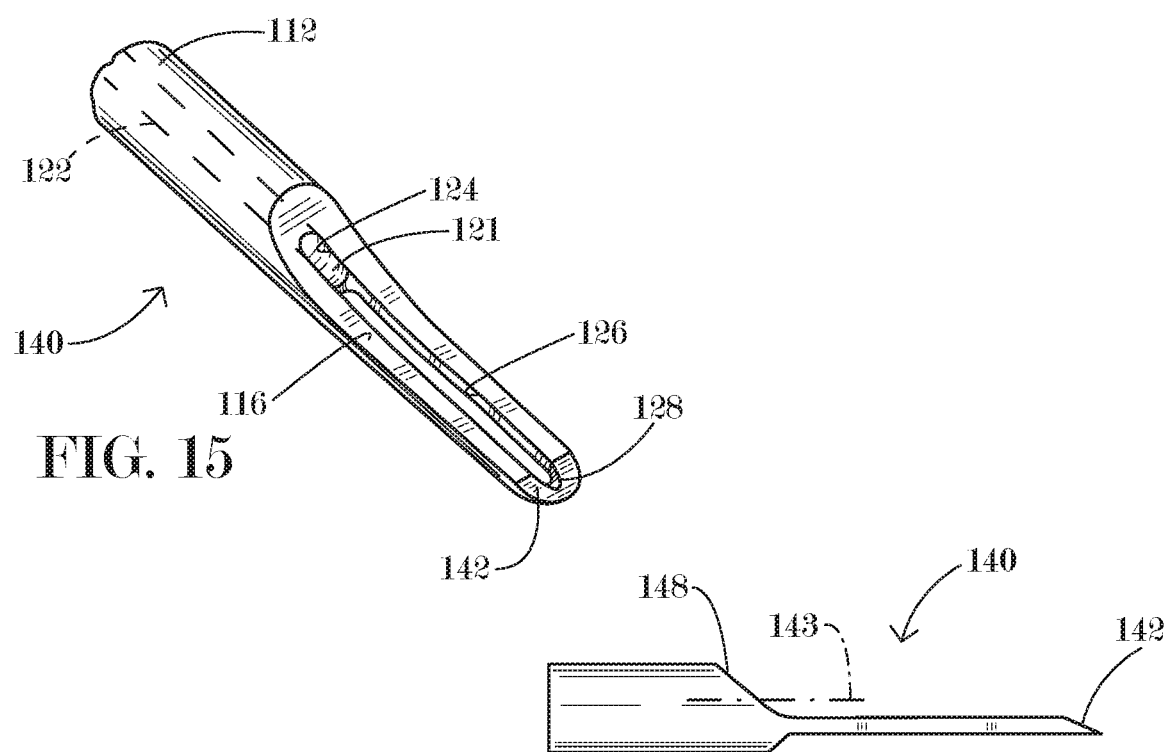
FIG. 15 is an isometric view of a distal end portion of yet a further ultrasonic surgical instrument or probe pursuant to the present invention.
FIG. 16 is a side elevational of the distal end portion of FIG. 15.

FIGS. 15 and 16 depict a surgical instrument 140 that is identical to instrument 110 except for a beveling at the distal end of the instrument. Reference numbers in FIGS. 15 and 16 are the same as those designating like features or elements of surgical instrument 110 in FIGS. 13 and 14. Instrument 140 has a beveled end surface 142. Distal groove section 128 is truncated by the formation of beveled end surface 142 and exhibits a tapering which facilitates distribution of irrigant from slot 126 over beveled end surface 142.

It is evident that in each of the instrument embodiments disclosed herein, the instrument shaft 22, 62, 82, 112 has an end face 48, 144, 146, 148 contiguous with a proximal end of the blade 25, 64, 84, 114 and also has a channel or bore 50, 72, 92, 122 with an outlet 52, 74, 94, 114 in that end face. The blade 25, 64, 84, 114 may be provided in a major lateral surface or flat 44, 86, 116 with a groove 91, 104, 121 continuous with the channel or bore 50, 92, 122 at the outlet 52, 94, 114 thereof. The groove 91 may extend the length of the blade to a distal end of the blade. Alternatively, where the blade 24, 84, 114 is provided with a through slot or hole 102, 126, the groove includes a section 104, 121 extending from the outlet 94, 124 of the shaft channel or bore 92, 112 to a proximal side of the through slot or hole 102, 126. The blade 84, 140 may be provided at a distal end, opposite the shaft 82, 112, with a beveled surface 96, 142 inclined with respect to the axis 88, 143 (FIG. 16). Alternatively or additionally, the blade 24, 114 may be formed with an arcuate distal tip, where the distal tip has a circular or cylindrical surface with an axis oriented perpendicular to the shaft axis.

As discussed hereinabove with reference to FIG. 6, a method for manufacturing a unitary ultrasonic surgical instrument having a shaft portion 22, 62, 82, 112 and a blade portion 24, 64, 84, 114 at a distal of free end of the shaft comprises providing a tool blank 38 including an enlarged connector portion 26 at one end and a cylindrical shaft 40 at an opposite end and machining a distal end portion 42 of the cylindrical shaft on opposing sides thereof to form the shaft portion 22, 62, 82, 112 from the cylindrical shaft and to generate two opposing flats 44, 66, 86, 116 and 46, 70, 90, 120. The formation of the flats 44, 66, 86, 116 and 46, 70, 90, 120 realizes the blade portion 24, 64, 84, 114 as a planar shaft extension or end portion that may have at least one edge surface 34, 78, 98, 132 that is a cylindrical section continuous and coaxial with a cylindrical outer surface of the shaft portion 22, 62, 82, 112. The machining of the distal end portion 42 of the cylindrical shaft 40 of the tool blank 38 typically includes rotating cutting tool 49 about a rotation axis extending parallel to at least one of the flats 44, 66, 86, 116 (perpendicular to the plane of the drawing in FIG. 6). Distal end portion 42 of the cylindrical shaft 40 of the tool blank 38 may be further machined along edge surfaces 34, 78, 98, 132, for instance, to taper the blade portion 24, 64, 84, 114, that is to reduce the free-end width thereof.

The machining of the distal end portion 42 of the cylindrical shaft 40 typically includes forming an end surface 48, 144, 146, 148 of the shaft portion 22, 62, 82, 112 as a cylindrical section (not shown) having an axis parallel to the rotation axis of the tool 49 and one or both flats 44, 66, 86, 116 and 46, 70, 90, 120. Further machining, either with tool 49 or a different tool can be undertaken to form shaft end surfaces 48, 144, 146, 148 as flat or planer surfaces inclined with respect to shaft axes 28, 68, 88, 118.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for manufacturing a unitary ultrasonic surgical instrument having a shaft portion and a blade portion at a distal of free end of said shaft portion, said blade portion being unitary and continuous with said shaft portion, without an intervening joint, said method comprising:
   providing a tool blank including an enlarged connector portion at one end and a cylindrical shaft at an opposite end; and
   machining a distal end portion of said shaft on opposing sides thereof to form said shaft portion from said cylindrical shaft and to generate two opposing flats, thereby forming said blade portion as a planar shaft extension or end portion,
   wherein the machining of said distal end portion of said shaft on said opposing sides thereof includes forming said blade portion to have at least one edge or outer surface that is a cylindrical section continuous and coaxial with a cylindrical outer surface of said shaft portion, that has a common diameter therewith so that said blade portion has a width equal to said common diameter, and that extends from said shaft portion to a distal tip or free end of said blade portion and concomitantly of said unitary ultrasonic surgical instrument.

2. The method defined in claim 1 wherein the machining of said distal end portion of said cylindrical shaft includes rotating at least one cutting tool about a rotation axis extending parallel to at least one of said flats.

3. The method defined in claim 1 wherein said shaft is linear or straight, without bends.

4. The method defined in claim 3 wherein said enlarged connector portion and said shaft are colinear and share a longitudinal axis.

5. A method for manufacturing a unitary ultrasonic surgical instrument having a shaft portion and a blade portion at a distal of free end of said shaft portion, said blade portion being unitary and continuous with said shaft portion, without an intervening joint, said method comprising:
   providing a tool blank including an enlarged connector portion at one end and a cylindrical shaft at an opposite end; and
   machining a distal end portion of said shaft on opposing sides thereof to form said shaft portion from said cylindrical shaft and to generate two opposing flats, thereby forming said blade portion as a planar shaft extension or end portion, wherein said cylindrical shaft has a longitudinal bore or channel and wherein the machining of said distal end portion of said shaft includes machining said distal end portion of said shaft on each of said opposing sides at an angle to said axis to configure said distal end portion of said shaft with a closed end and a through hole or opening extending between said opposing flats.

6. A method for manufacturing a unitary ultrasonic surgical instrument having a shaft portion and a blade portion at a distal of free end of said shaft portion, said blade portion being unitary and continuous with said shaft portion, without an intervening joint, said method comprising:

providing a tool blank including an enlarged connector portion at one end and a cylindrical shaft at an opposite end; and machining a distal end portion of said shaft on opposing sides thereof to form said shaft portion from said cylindrical shaft and to generate two opposing flats, thereby forming said blade portion as a planar shaft extension or end portion, wherein said cylindrical shaft has a longitudinal bore or channel and wherein the machining of said distal end portion of said shaft includes machining said distal end portion of said shaft on each of said opposite sides at an angle to said axis to configure said distal end portion of said shaft with (i) a closed end, (ii) a through hole or opening extending between said opposing flats, (iii) a first groove extending on one of said opposing flats between a distal end of said shaft portion and said through hole or opening, and (iv) a second groove on another one of said opposing flats on a distal side thereof opposite said shaft portion.

7. A method for manufacturing a unitary ultrasonic surgical instrument, said method comprising:

providing a tool blank including an enlarged connector portion at one end and a cylindrical shaft at an opposite end, said enlarged connector portion and said shaft being co-linear and sharing a longitudinal axis; and machining a distal end portion of said shaft on opposing sides thereof to form a shaft portion of said instrument from said cylindrical shaft and to generate two opposing flats or planar major surfaces, thereby forming a flat or planar blade portion of said instrument, so that said blade portion is unitary and continuous with said shaft portion, without an intervening joint, and so that said blade portion has a proximal end eccentrically disposed relative to said axis, extends at an angle with respect to said axis and intersects said axis, and has at least one edge or peripheral surface in the form of an endless cylindrical section or perimetral outer surface continuous and coaxial with a cylindrical outer surface of said shaft portion.

8. The method defined in claim 7 wherein the machining of said distal end portion of said cylindrical shaft includes rotating at least one cutting tool about a rotation axis extending parallel to at least one of said flats.

* * * * *